United States Patent [19]
Rathburn et al.

[11] Patent Number: 5,672,680
[45] Date of Patent: Sep. 30, 1997

[54] PENTACLETHERA MACROLOBA PROTEIN HAVING INSECTICIDAL PROPERTIES

[75] Inventors: Harold B. Rathburn, Norman, Okla.; Thomas H. Czapla, Urbandale, Iowa; Karel R. Schubert, Norman, Okla.

[73] Assignee: Pioneer Hi-Bred International, Inc., Des Moines, Iowa

[21] Appl. No.: 560,727

[22] Filed: Nov. 20, 1995

[51] Int. Cl.$^6$ .................... A61K 38/04; A61K 38/00; A61K 35/78; C07K 1/00
[52] U.S. Cl. .................... 530/300; 514/10; 530/350; 530/370; 530/379
[58] Field of Search .................... 530/300, 370, 530/350, 379; 514/12

[56] References Cited

PUBLICATIONS

Kngsley, Mbajunwa Obinna; "Effect of Processing on Some Antinutritive and Toxic Components and on the Nutritional Composition of the African Oil Bean Seed "(*Pentaclethra macrophylla* Benth); *J Sci Food Agric* 1995, 68, 153–156.

Negreiros, Andre N. Monte, et al.; "The Complete Amino Acid Sequence of the Major Kunitz Trypsin Inhibitor from the Seeds of *Prosopsis Juliflora*" *Phytochemistry;* vol. 30, No. 9 pp. 2829–2833 (1991).

Wu, Han–Chung, et al.; "The Complete Amino Acid Sequence of a Kunitz Family Trypsin Inhibitor from Seeds of *Acacia confusa*"; *J. Biochem.* 113, 258–263 (1993).

Negreiros, Andre N. Monte, et al.; "The Complete Amino Acid Sequence of the major Kunitz Trypsin Inhibitor from the Seeds of *Prosopsis Juliflora*" *Phytochemistry;* vol. 30, No. 9 pp. 2829–2833 (1991).

Yamamoto, Masashi, et al.; "Amino Acid Sequence of Two Trypsin Inhibitors from Winged Bean Seeds" (*Psophocarpus tetragonolobus* (L) DC.); *J. Biochem.* 94, 849–863 (1983).

Kim, Seung-Ho, et al.; "Comparative Study on Amino Acid Sequences of Kunitz-Type Soybean Trypsin Inhibitors, $Ti^a$, $Ti^b$, and $Ti^{cn}$; *J. Biochem.* 98, 435–448 (1985).

Richardson, M., et al.; "The Amino Acid Sequence and Reactive (Inhibitory) Site of the Major Trypsin Isoinhibitor (DE5) Isolated from Seeds of the Brazilian Carolina Tree (*Adenanthera pavonina* L.)"; *Biocimica of Biophysica Acta* 872 134–140 (1986).

Ryan, Clarence A.; "Protease Inhibitors in Plants: Genes for Improving Defenses Against Insects and Pathogens", *Annu. Rev. Phytopathol.* 28:425–429 (1990).

Chun, et al. Pentaclethra macroloba Seed Effect on Larval Gowth, Cell Viability, and Midgut Enzyme Acitivty of *Helicoverpa zea* (Lepidoptera: Noctuidae), Journal of Economic Entomology, vol. 87, No. 6, pp. 11754–1760. Dec. 1994.

*Primary Examiner*—Cecilia J. Tsang
*Assistant Examiner*—Jennifer Harle

[57] ABSTRACT

The invention comprises purified trypsin inhibitors extracted from the seeds of *Pentaclethra macroloba*. The crude extract was found to comprise two molecular weight ranges of 38–35 and 6–9 kDa which contain the active compounds. Within each molecular weight range, the trypsin inhibitors were found to exist in two isoforms. The lower molecular weight inhibitor exhibits surprising stability and activity after heating in aqueous solution at approximately 100° C. for 30 minutes.

9 Claims, 3 Drawing Sheets

PENTACLETHERA MACROLOBA PROTEIN HAVING INSECTICIDAL PROPERTIES

FIELD OF THE INVENTION

The invention relates to methods and materials for controlling insect species. In particular, the invention relates to identified compounds extracted from the plant *Pentaclethra macroloba*, which compounds exhibit insecticidal activity via trypsin inhibition or other mechanisms.

BACKGROUND OF THE INVENTION

Numerous insect species are serious pests to common agricultural crops such as corn, soybeans, peas and similar crops. During the last century, the primary method of controlling such pests has been through the application of synthetic chemical insecticide compounds. However, as the use of such chemical compounds proliferated and continued, it became evident that such wide-spread use posed problems with regard to the environment, the non-selectivity of the compounds, increasing insect resistance to the chemicals and the effect of such compounds, after run-off, on higher order species such as fish and birds among others. As a result of such problems, other methods of controlling insect pests were sought and tried.

One such alternative method of pest control has been the use of biological organisms which are typically "natural predators" of the species sought to be controlled. Such predators may include other insects, fungi (milky-spore) and bacteria such as *Bacillus thurengiensis* cv. Alternatively, large colonies of an insect pest have been captively raised, sterilized and released into the environment in the hope that mating between the sterilized insects and fecund wild insects will decrease the insect population. While both these approaches have had some success, they entail considerable expense and present several major difficulties. For example, it is difficult both to apply biological organisms to large areas and to cause such living organisms to remain in the treated area or on the treated plant species for an extended time. Predator insects can migrate and fungi or bacteria can be washed off a plant or removed from a treated area by rain. Consequently, while the use of such biological controls has desirable characteristics and has met with some success, in practice these methods seem severely limited. However, scientific advances seem to offer new opportunities for controlling insect pests.

The advances in biotechnology in the last two decades has presented new opportunities for pest control through genetic engineering. In particular, advances in plant genetics coupled with the identification of insect growth factors and naturally occurring plant defensive compounds or agents offer the opportunity to create transgenic crop plants capable of producing such defensive agents to thereby protect the plants against insect attack.

Scientists have identified some specific plant components or compounds which act as defensive agents to protect a plant from attack by insect pests and pathogens. While such components are usually present at only low levels in various plant tissues, some of them are also capable of being induced to higher levels upon attack by an insect pest or a pathogen. Examples of such defensive compounds include alkaloids, terpenes and various proteins such as enzymes, enzyme inhibitors and lectins (1, 4, 13 and 30). Of particular interest are enzyme inhibitors which can block enzymatic activity and inhibit insect growth. For example, trypsin is a digestive enzyme secreted by the pancreas into the small intestine. Its role in a body is to hydrolyze polypeptides into smaller units which can then be utilized by the host subject, for example, an insect. An enzyme such as trypsin which catalyzes the hydrolysis of peptide bonds is called a protease. Blocking trypsin activity will inhibit insect growth. A trypsin inhibitor (abbreviated TI) is thus a compound, typically a protein compound, which will block or decrease trypsin protease activity. As a result of such blockage or decrease in trypsin protease activity, a host subject which has ingested TI with its food will obtain little or no benefit from the polypeptides contained in the food. The host may thus fail to grow, mature and may indeed ultimately starve and die.

Ryan et al. (30) have reported on the presence of proteinaceous trypsin inhibitors and lectins in the seeds of a number of leguminous tropical plants and have suggested that these proteins may play a role in the plant's defenses against insect attack. The proposed role of such trypsin inhibitors (TIs) in plant defense has been shown using transgenic plants expressing a TI gene. Hilder et al. (11) introduced the Bowman-Birk TI gene from soybeans into tobacco plants and showed that the transgenic plants were able to resist damage from a lepodopteran insect. Transformation and expression of other TI genes such as potato TI I and II also resulted in transgenic plants which showed resistance to insect attack. However, transgenic plants which contained an unexpressed TI gene were susceptible to insect attack (15). Consequently, in order to have pest protection, a plant must not only contain the protective gene, but it must also express it: that is, the TI gene must be producing, or capable of producing upon pest attack, the inhibitor or defensive agent.

The choice of trypsin inhibitor compound to be transgenically inserted into a plant species is crucial to effective pest control. Belitz et al. (2) and Christeller et al. (5) have shown that TIs obtained from different plant species have considerably different inhibitive constants ($K_i$ values). Consequently, prior to genetic transformation of a crop species, it is necessary to screen TIs from a variety of plant sources in order to identify those having sufficiently strong activity so that the transgenic crop plant will have sufficient resistance to insect attack. For purposes of identifying such TIs, it is noted that except for inducible inhibitors, most protease inhibitors are located in plant storage organs such as seeds and tubers.

An ideal source of plant species to investigate for potential TIs is the tropical rain forest. The diversity of plant and insect life provides an ideal evolutionary background for the development of TIs. For example, a given tropical plant species might be the subject of attack by a variety of insect species. Consequently, the plant may develop a particularly strong or effective TI for use as a protective agent against such a diversity of insect life. Janzen et al. (14) investigated seeds from 59 legumes and showed that while all were capable of inhibiting bovine trypsin, they did so at different levels; that is, some were stronger inhibitors than others. One such tropical rain forest plant not tested by Jenzen was the legume *Pentaclethra macroloba* (hereinafter *P. macroloba* or Pm, (10)). *P. macroloba* seed extracts were shown to reduce insect growth, and the investigators suggested, without identifying the active species, that the growth inhibition might be due to trypsin inhibition, lectin or both. More recently, Chun et al. (6) showed that aqueous seed extracts from *P. macroloba* had an inhibitory effect on insect herbivores.

The purpose of the present invention is to identify and characterize trypsin inhibitors obtainable from *P. macroloba* which reduce insect growth and increase insect, particularly larval, mortality.

It is a further purpose of the invention to provide a method for the separation and isolation of trypsin inhibitors obtainable from *P. macroloba* and to demonstrate the inhibitory nature of such inhibitory compounds.

It is a further purpose of the invention to identify a trypsin inhibitor which has sufficient insect growth inhibitory effects to warrant its being transgenically inserted into a food crop gene where it will be expressed and will provide protection from one or a plurality of insect species including, but not limited to, European corn borer (*Ostrinia nubilalis*), Diabrotica species such as the Western, Southern and Northern corn rootworms, corn earworm (*Helicoverpa zea*), cowpea weevil (*Callosobruchus maculatus*) and similar insect pests known to those skilled in the art.

It is a further purpose of the invention to identify a trypsin inhibitor which retains its inhibitory ability after aqueous heating at approximately 100° C. for approximately 30 minutes.

It is a further purpose to provide the amino acid sequence of one or a plurality of trypsin inhibitors obtainable from *P. macroloba*.

SUMMARY OF THE INVENTION

The invention identifies and provides trypsin inhibitors obtainable from *Pentaclethra macroloba*, said inhibitors being approximately 38–45 and 6–9 kilodaltons (kDa) in size, wherein said 38–45 kDa species comprises of a 43 kDa species having a N-terminus designated 5B and comprising Sequence ID. No. 1: Glu-Val-Val-Phe-Asp-Phe-Lys-Gly-Asp-Met-Met-Arg-Asn-Gly-Gly-His-Tyr-Tyr-Phe-Phe-Pro-Ala-Ala-Pro-Tyr-Gly-Gly-Gly-Asn-Leu-Leu-Ala-Ala-Ala-Val (shortened nomenclature:

EVVFDFKGDMMRNGGHYYFFPAAPYGGGNLLAAAV).

The invention is also directed to a purified trypsin inhibitor obtained from *Pentaclethra macroloba* comprising the steps of extracting sliced seeds from said *Pentaclethra macroloba*, extracting said sliced seeds with water to obtain a crude extract and purifying the crude extract to obtain a trypsin inhibitor comprising a plurality of active components whose molecular weights are in the ranges of 38–45 and 6–9 kDa.

The invention is further directed to a process for protecting plants against insect attack by European corn borer, *Helicoverpa Zea*, corn rootworms and similar insects comprising exposing said insects to an insecticidal protein obtained from *P. macroloba*, said insecticidal protein being contained within a crude or purified extract of *P. macroloba* seed and identified as having a plurality of active components whose molecular weights are in the ranges of 38–45 and 6–9 kDa; wherein said 38–45 kDa species consists of a 43 kDa species having a N-terminus designated 5B and comprises Sequence ID. No. 1: Glu-Val-Val-Phe-Asp-Phe-Lys-Gly-Asp-Met-Met-Arg-Asn-Gly-Gly-His-Tyr-Tyr-Phe-Phe-Pro-Ala-Ala-Pro-Tyr-Gly-Gly-Gly-Asn -Leu-Leu-Ala-Ala-Ala-Val (shortened nomenclature: EVVFDFKGDMMRNGGHYYFFPAAPYGGGNLLAAAV).

DETAILED DESCRIPTION OF THE INVENTION

References

Figure 1:
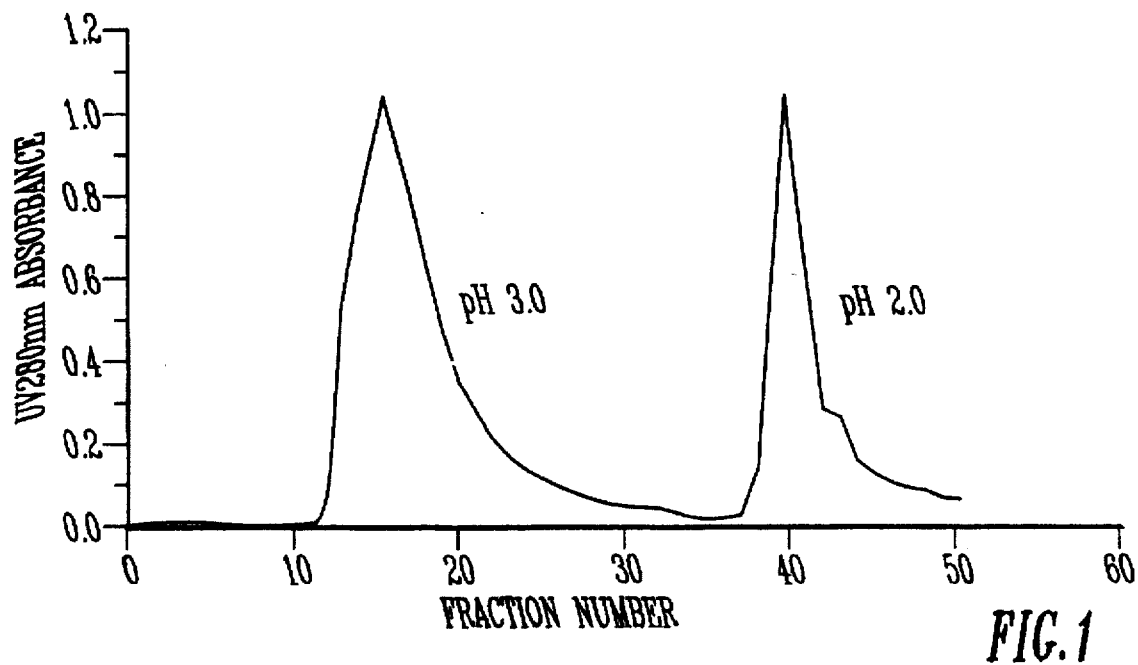
FIG. 1 illustrates an affinity chromatogram of the isolated trypsin inhibitors obtained from *P. macroloba* in accordance with the invention.

The teachings of the following publications are incorporated herein by reference.

1. L. T. Baldwin, *Oecologia* 75: 367–370 (1989).
2. H. D. Belitz et al., *Z. Lebensm. Unters.-Forsch* 4: 442–446 (1982).
3. C. W. Chi et al., *Biol. Chem. Hoppe-Seyler* 6: 879 (1985).
4. M. J. Chrispeel et al., *Plant Cell* 3: 1–9 (1991).
5. J. T Christeller et al., *Insect Biochem.* 233–241 (1989).
6. J. Chun et al., *J. Econo. Ento.* 87: 1754–1760 (1994).
7. D. E. Fahrney et al., *J. Amer. Chem. Soc.* 997–1000 (1963).
8. F. Garcia-Olmedo et al., *Oxf. Surv. Plant Mol. and Cell Biol.* 4: 275–334 (1987).
9. B. C. Hammer et al., *Phytochemistry* 3019–3026 (1989).
10. G. S. Hartshorn in *Costa Rica Natural History*, Janzen Ed. (Univ. Chicago Press, Chicago 1983), pages 301–303.
11. V. A. Hilder et al., *Nature* 330: 160–163 (1987).
12. D. L. R. Hwang et al., *Biochim. Biophys. Acta* 495: 369–382 (1977).
13. D. H. Janzen et al., *Phytochemistry* 223–227 (1977).
14. D. H. Janzen et al., *J. Chem. Ecol.* 12: 1469–1480 (1986).
15. R. Johnson et al., *Proc. Natl. Acad. Sci.* 86: 9871–9875 (1989).
16. F. J. Joubert, *Phytochemistry* 22: 53–57 (1983).
17. S. H. Kim et al., *Blochem.* 98: 435–448 (1985).
18. A. A. Kortt et al., *Eur. J. Biochem.* 115: 551–557 (1981).
19. U. K. Laemmli, *Nature* 227: 680–685 (1970).
20. M. Laskowski et al., *Ann. Rev. Biochem.* 49: 593–626 (1980).
21. A. N. Negreiros et al., *Phytochemistry* 30: 2829–2833 (1991).
22. S. Odani et al., *J. Biochem.* 80: 641–643 (1976).
23. S. Odani et al., *J. Biochem.* 70: 925–936 (1971).
24. S. Odani et al., *J. Biochem.* 86: 1795–1805 (1979).
25. G. Pearce et al., *Plant Physiol.* 102: 639–644 (1993).
26. T.-C. Pham et al., *Biol. Chem. Hoppe-Seyler* 366: 939–944 (1985).
27. A. Pustzai et al., *Anal. Biochem.* 172: 108–112 (1988).
28. H. Rathburn et al., *J. Econo. Ento.* (submitted).
29. M. Richardson et al., *Biochim. Biophys. Acta.* 872: 134–140 (1986).
30. C. A. Ryan, *Ann. Rev. of Phytopathol.* 28: 425–449 (1990).
31. J. Ureil et al., *Nature* 218: 578–580 (1968).
32. H. C. Wu et al., *J. Biochem.* 113: 258–263 (1993).
33. M. Yamamoto et al., *J. Blochem.* 94: 849–863 (1983).
34. C. J. Lenz et al., *Arch. Insect Biochem Physiol.* 16: 201–212 (1991).
35. W. R. Terra et al., *J. Insect Physiol.* 25: 487–494 (1979).
36. Y. Takesue et al., *J. Biochem.* 105: 998–1001 (1989).
37. S. E. McEwen et al., *Insect Biochem.* 10: 563–567 (1980).

38. J. F. Myrtle and W. J. Zell, *Clin. Chem.* 21: 1469–1473 (1980).
39. K. K. Thomas and J. L. Nation, *Comp. Biochem. Physiol. A Comp. Physiol.* 79: 297–304 (1984).
40. T. H. Czapla and B. A. Lang, *J. Econo Ento.* 83 (6): 2480–2485 (1990).

Terminology and Abbreviations

1. TI=trypsin inhibitor.
2. pI=the pH of a solution containing a molecule at which there is no charge on that molecule.
3. IEF=Iso-electric focusing.
4. SDS-PAGE=Sodium dodecyl sulfate—Polyacrylamide gel electrophoresis.
5. NaOAc=sodium acetate
6. Tris-Cl=Trizma base molecular biology reagent.
7. FPLC=HPLC (high pressure liquid chromatography).
8. BAPNA=A synthetic substrate used to show trypsin cleavage and detect inhibition of the trypsin enzyme.
9. PMFS=phenylmethylsulfonylfluoride, a compound which reacts with serine residues.
10. PmTI=*P. macroloba* trypsin inhibitors generally or a mixture comprising PmLTI and PmSTI.
11. PmLTI=*P. macroloba* large trypsin inhibitor, molecular weight range 38–45 kDa.
12. PmSTI=*P. macroloba* small trypsin inhibitor, molecular weight range 6–9 kDa.
13. AC=Acacia Confusa TI (Ref. 32). Amino Acid Sequence ID. No. 2: Lys-Glu-Leu-Leu-Asp-Ala-Asp-Gly-Asp-Ile-Leu-Arg-Asn-Gly-Gly-Ala-Tyr-Tyr-Ile-Leu-Pro-Ala-Leu-Arg-Gly-Lys-Gly-Gly-Gly-Leu-Thr-Leu-Ala-Lys-Thr (shortened nomenclature: KELLDADGDILRNGGAYYILPALRGKGGGLTLAKT).
14. PJ=*Prosopsis jukiflora* TI (Ref. 21). Amino Acid Sequence ID. No. 3: Gln-Glu-Leu-Leu-Asp-Val-Asp-Gly-Glu-Ile-Leu-Arg-Asn-Gly-Gly-Ser-Tyr-Tyr-Ile-Leu-Pro-Ala-Phe-Arg-Gly-Lys-Gly-Gly-Gly-Leu-Glu-Leu-Ala-Lys-Thr (shortened nomenclature: QELLDVDGEILRNGGSYYILPAFRGKGGGLELAKT).
15. WB=WInged bean TI (Ref. 33). Amino Acid Sequence ID. No. 4: Glu-Pro-Leu-Leu-Asp-Ser-Glu-Gly-Glu-Leu-Val-Arg-Asn-Gly-Gly-Thr-Tyr-Tyr-Leu-Leu-Pro-Asp-Arg-Trp-Ala-Leu-Gly-Gly-Gly-Ile-Glu-Ala-Ala-Ala-Thr (shortened nomenclature: EPLLDSEGELVRNGGTYYLLPDRWALGGGIEAAAT).
16. SB=Soybean TI (Ref. 17). Amino Acid Sequence ID. Nos. 5 and 7: Asp-Phe-Val-Leu-Asp-Asn-Glu-Gly-Asn-Pro-Leu-Glu-Asn-Gly-Gly-Thr-Tyr-Tyr-Ile-Leu-Ser-Asp-Ile-Thr-Ala-Phe and Gly-Gly-Ile-Arg-Ala-Ala-Pro-Thr (shortened nomenclature: DFVLDNEGNPLENGGTYYILSDITAF-GGIRAAPT).
17. Ap=Adenanthera Pavonina TI (Ref. 29). Amino Acid Sequence ID. No. 6: Arg-Glu-Leu-Leu-Asp-Val-Asp-Gly-Asn-Phe-Leu-Arg-Gly-Gly-Ser-Tyr-Tyr-Ile-Val-Pro-Ala-Phe-Arg-Gly-Lys-Gly-Gly-Gly -Leu-Glu-Leu-Ala-Arg-Thr-Gly (shortened nomenclature: RELLDVDGNFLRGGSYYIVPAFRGKGGGLELARTG).

*P. macroloba* seeds were collected at the La Selva Biological Station, Costa Rica and transported to the inventor's laboratories where they were sliced, lyophilized and stored at −20° C. prior to use. Seed extract was prepared as described by Rathburn et al. (28) with and without heating as noted herein. Heating was accomplished by boiling sliced seeds in 0.1M Tris-Cl, pH 8.5, 5 mM $MgCl_2$ before homogenization.

Both trypsin and anhydrotrypsin affinity chromatography, designated TAC and ATAC respectively, were used to isolate trypsin inhibitors from crude extracts. TAC was performed according to the method of Rathburn (28). Anhydrotrypsin was prepared according to the method of Pusztal (27) until the trypsin activity was less than 0.5%. Anhydrotrypsin was coupled to cyanogen bromide activated Sepharose 4B according to the manufacturer's instructions (Pharmacia). Chromatography columns were equilibrated with 0.1M Tris-Cl, pH 8.5, 5 mM $MgCl_2$, 3 mM PMFS. Proteins that were bound to the column were eluted with 0.5M NaOAc buffer containing 0.5M NaCl by decreasing the pH from 7.0 to 2.0. Absorbance at 280 nm (nanometers) was used to follow the elution of the bound proteins. Fractions that inhibited bovine trypsin were pooled, dialyzed and lyophilized.

Size exclusion chromatography (SEC) was performed at room temperature, 18°–28° C., on affinity purified trypsin and anhydrotrypsin fractions. A 1.5×100 cm (centimeter) column of Sephadex G-50 was equilibrated with 50 mM NaOAc, 0.25M NaCl, pH 5.0. Two to five milligrams (mg) of affinity purified trypsin inhibitor was applied to the column and separated at a flow rate of 15 ml/hr. 2.5 ml fractions were collected. Alternatively, trypsin protein was separated by HPLC on a Superose 12 column. Samples were heated at 100° C. for 5 minutes in the presence of 2 mM 2-mercaptoethanol prior to application to the column. The column was equilibrated with degassed 50 mM sodium phosphate buffer, pH 7.0, 0.15M NaCl. The flow rate was controlled at 0.5 ml/min. 0.5 ml fractions were collected for 20–60 minutes. Fractions which exhibited trypsin activity were pooled and dialyzed against water.

Ion exchange chromatography was used to separate large (high molecular weight) trypsin inhibitors from other fractions. Large TIs were separated on a 1.5 ×5 cm anion exchange column containing BioRad Q5 which had been equilibrated with 40 mM ethanolamine-HCl, pH 9.5. TIs were eluted using a linear gradient from 0 to 0.15M NaCl. Two milliliter fractions were collected, tested for inhibition of bovine trypsin and absorbance at 280 nm was measured.

Crude *P. macroloba* extracts were extensively dialyzed against deionized water at 4° C. for several days using a technique combining two molecular weight cutoff (MWCO) membranes or tubings (3,500/10,000 or 3,500/14,000). The higher limit MWCO membrane or tubing contained the crude extract and was placed inside the 3,500 membrane. Deionized water was changed at 12 hour intervals. The separated fractions outside the higher MWCO membrane were collected and affinity chromatographed. When desired, the same tubing combinations can be used to separate affinity purified trypsin inhibitors. Fractions from SEC could also be dialyzed against water using different MWCO membranes.

SDS-PAGE was used to separate components and determine their molecular weights. The procedure was carried out according to the method of Laemmli (19) using two types of gel, a 12–15% acrylamide gel or a 10–20% gradient acrylamide gel. Protein samples were denatured by boiling for three minutes in SDS buffer (BioRad) with 2 mM 2-mercaptoethanol. Selective samples, referred to herein as native samples, were not boiled prior to electrophoresis. The estimated molecular weights of native and denatured trypsin inhibitors were determined by electrophoresis on gradient SDS-PAGE gels of 10–20% polyacrylamide under conditions given by Hammer (9). Proteins were detected by staining with Commassie Brilliant Blue R-250 (CBB R-250). Inhibitory activity was detected using the assay of Ureil and Berges (31) as modified by Rathburn (25).

Trypsin activity was determined as described by Rathburn (28). The activity of the inhibitors is expressed in Inhibition Units (IU), where 1 IU is the amount of inhibitor needed to reduce BAPNA ($e=8.8$ $mmol^{-1}cm^2$) hydrolysis by 1 mmol/min at 25° C.

FIG. 1 illustrates the use of affinity chromatography to isolate trypsin inhibitor(s) from P. macroloba. A crude extract was brought directly to a 1×20 cm column and washed until the flow absorbance was less than 0.02 at 280 nm. The column was then eluted using 0.5M NaOAc, 0.5M NaCl buffer from pH 2.0 to 7.0 and fractions collected.

Figure 2A:
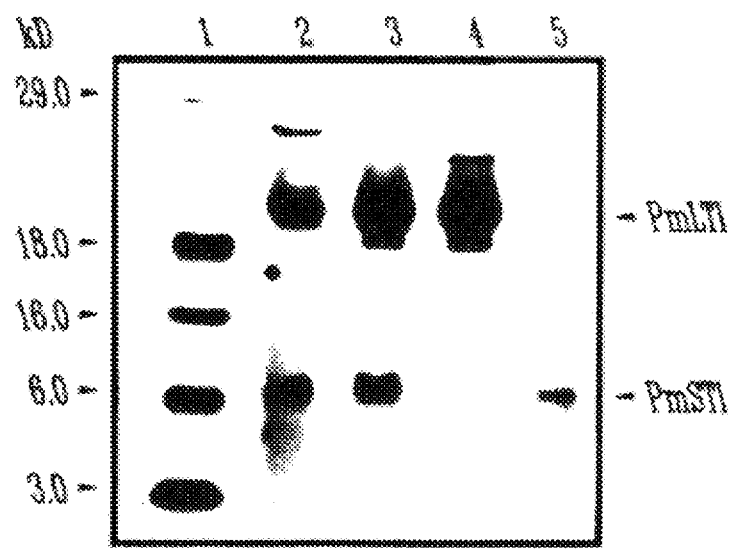
FIG. 2A illustrates the SDS-PAGE separation of *P. macroloba* trypsin inhibitors in accordance with the invention.
Figure 2B:
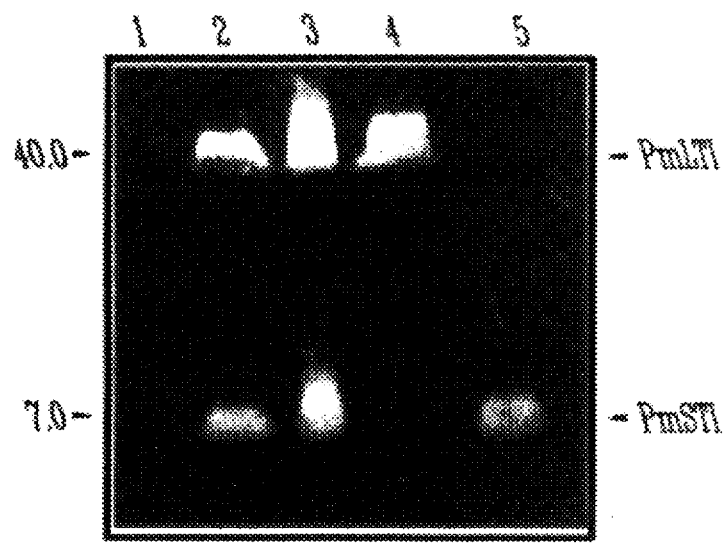
FIG. 2B illustrates in-gel trypsin inhibitory activity staining.

FIGS. 2A and 2B illustrate SDS-PAGE of P. macroloba inhibitors. In FIG. 2A, a silver stain was used. The sample was mixed with non-reducing buffer (BioRad) and heated for 3 minutes at 100° C. prior to electrophoresis.

FIG. 2B illustrates in-gel inhibitory activity staining. A sample was mixed with with non-reducing sample buffer and was not heated. The lanes represent the following: Lane 1, molecular weight markers; Lane 2, crude Pm extract; Lane 3, affinity purified PmTI; Lane 4, PmLTI; and Lane 5, PmSTI.

FIG. 1 illustrates the two major peaks that were isolated from TAC using pH 3.0 and 2.0 buffers. The pH 2.0 fraction was identified as denatured protein and did not inhibit trypsin activity. The pH 3.0 fraction contains two classes of trypsin inhibitors designated herein as P. macroloba large trypsin inhibitor (PmLTI) and P. macroloba small trypsin inhibitor (PmSTI) as shown in FIGS. 2A and 2B. In addition, several additional polypeptides were obtained. Tests were conducted to determine whether PmLTI was cleaved by trypsin during purification and whether PmSTI was a portion of the degraded PmLTI. Crude extracts were subject to electrophoresis, and inhibition activity was determined using an in-gel trypsin inhibition assay. Two trypsin inhibitors of the same mobility as that of the affinity purified pH 3.0 fraction were detected as shown in FIG. 2. These results indicate that two different trypsin inhibitors, PmLTI and PmSTI, exist in P. macroloba seeds.

ATAC was used to determine whether PmSTI and the additional polypeptides seen in TAC were the result of cleavage of PmLTI by fully active trypsin during affinity chromatography. In this assay, the active site of trypsin was blocked. Trypsin inhibitor isolated by ATAC was considered to be without modification (27). Five bands were observed on the SDS-PAGE of PmTI isolated by this procedure and reduced. In contrast, heat denatured PmTI showed only one band of Mr=21.5 kDa (data not shown). By comparison to the PmTI isolated from the fully active trypsin affinity column, it was concluded that PmTI was degraded by trypsin during affinity chromatography purification.

Further analysis of native, denatured and reduced PmTIs indicate the PmLTI consists of two isoinhibitors, each composed of two subunits without association by a disulfide bridge. One of the subunits is believed to possess two chains linked by a disulfide bridge.

PmSTI/PmLTI ratio was found to be very low. In the affinity purified products, PmSTI could not be detected in stained SDS-PAGE gel despite the fact that in-gel inhibition assay gave a large clear spot for this inhibitor.

Figure 3:
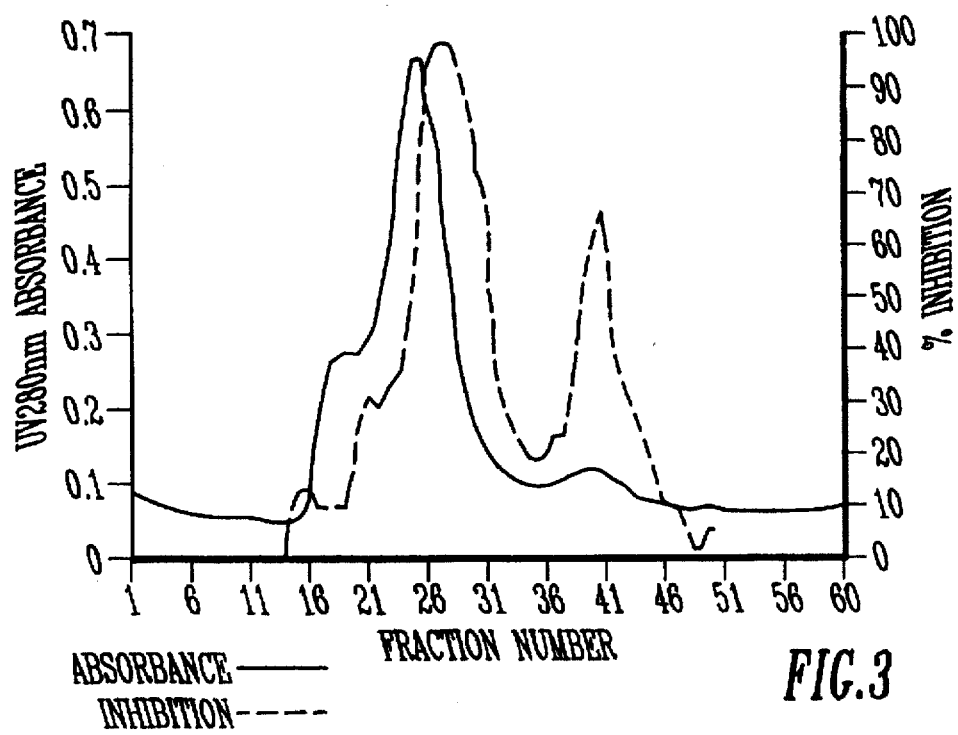
FIG. 3 illustrates the separation by Sephadex G-50 of two types of trypsin inhibitors obtained in accordance with the invention.

FIG. 3, gel filtration on Sephadex G-50 carried out at pH 5.0, shows two well-separated peaks corresponding to PmLTI and PmSTI. SDS-PAGE results indicate that peak I is purified PmLTI and peak II is PmSTI, admixed with a small amount of inactive PmLTI, whose activity was detected by the in-gel assay of FIG. 2.

Figure 4:
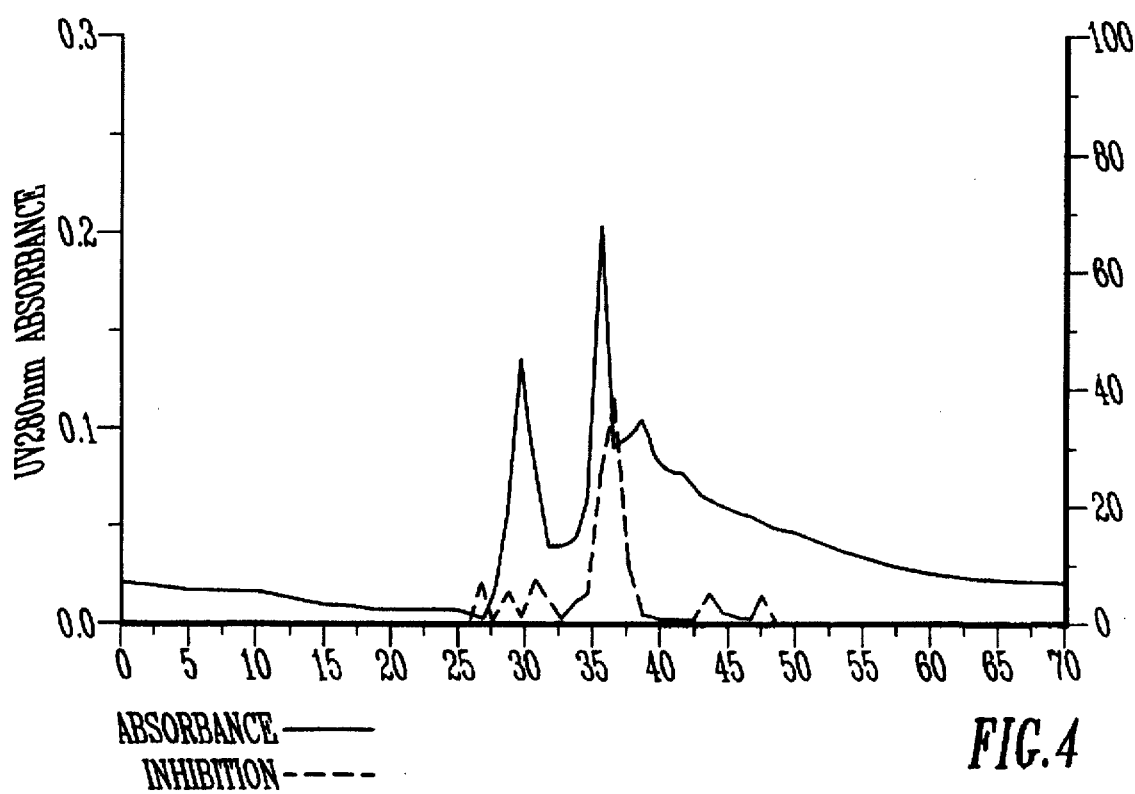
FIG. 4 illustrates the separation by HPLC of a trypsin inhibitor mixture obtained according to the invention and heat treated for 3 minutes by boiling in aqueous solution.

FIG. 4 illustrates the separation of heat-treated PmTI by HPLC. An aqueous sample was boiled for 3 minutes, applied to a Superose column and eluted.

Figure 5:
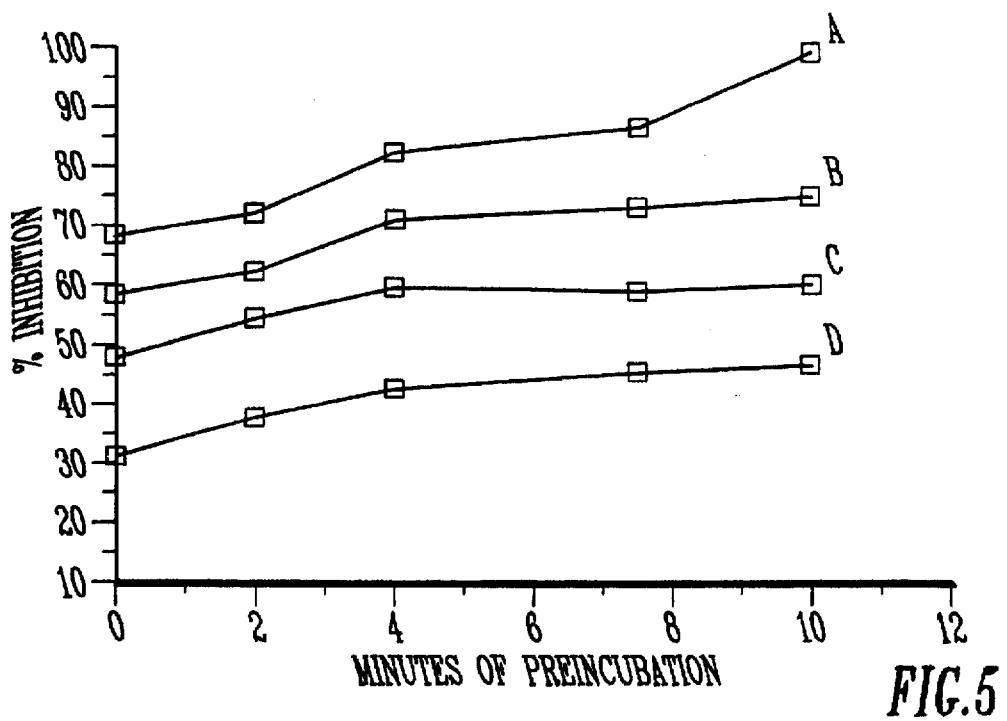
FIG. 5 illustrates an inhibition assay trypsin and *P. macroloba* trypsin inhibitors in BAPNA substrate incubated over time.

FIG. 5 is an inhibition assay, over incubation time, of samples containing trypsin and PmTI. Samples were prepared using a solution of 0.1M Tris-Cl, pH 9.5. The samples (A, B, C, and D) contained 5 mg trypsin and PmTI amounts of: (A) 18 nanograms, (B) 14.4 nanograms, (C) 10.8 nanograms and (D) 7.2 nanograms. BAPNA substrate in the amount of 2.5 mM was added to each sample. Trypsin activity was measured at various time points after the addition of the BAPNA substrate.

In order to fully understand the chromatographic behavior of both PmLTI and PmSTI, reduced and native affinity purified trypsin inhibitors were separated over a SEC column. Protein profiles with and without reduction were similar, indicating that the dimer is not linked by one or more disulfide bridges. The heat stability of PmSTI, discussed below, can be used to distinguish PmSTI from PmLTI and other trypsin inhibitors. A sample of PmSTI was heat treated, chromatographed on a SEC column and showed three product peaks. Only peak II was active, indicating that this peak corresponds to PmSTI. Peak III was close in molecular weight to Peak II, but did not exhibit any inhibition activity.

PmSTI is a small polypeptide in the 6–9 kDa range, generally about 7 kDa molecular weight, and is present in low concentrations in P. macroloba seeds. Large quantities of PmSTI can be obtained by first dialyzing crude extracts in tubing of 12–14 kDa MWCO. PmSTI, along with other low molecular weight proteins, dialyzed out of the 12–14 kDa membrane and was collected within a 3,500 MWCO membrane. The PmSTI fraction was further purified by affinity chromatography followed by gel filtration.

The molecular weight of the trypsin inhibitors was determined by 10–20% SDS-PAGE. The two iso-inhibitors (isoforms) constituting PmLTI were found to have molecular weights of approximately 43 and 39 kDa. Denaturing the PmLTI fraction by heating converted it into a species having a molecular weight of about 21.5 kDa. In-gel trypsin inhibition assay of PmLTI indicates that it is composed of two active proteins of pI 8.8 and 8.5. Similar testing of PmSTI indicates it is a low molecular weight polypeptide having a molecular weight of about 7 kDa and contains two active proteins of pI 8.2 and 5.0. [Data not shown]. These results indicate both PmLTI and PmSTI contain two iso-inhibitors of nearly the same molecular weight.

Heating affinity purified P. macroloba TIs has a profound effect on their inhibition activity. A crude extract, containing both PmLTI and PmSTI, had an inhibition activity of 2.2 IU/mg TI before heating and 3.7 IU/mg TI after heating at 70° C. The extract thus lost 40% of its inhibition activity upon heating. Further tests of purified PmLTI and PmSTI fractions indicates that PmLTI partially loses it activity after heating at 70° C. and completely loses activity after heating at 100° C. for 5 seconds. In contrast, PmSTI retained activity after boiling at 100° C. for 30 minutes. PmSTI did lose activity after boiling for 5 minutes under reducing conditions.

Amino Acid Sequence Information

The N-terminal sequence of PmLTI has been determined and is shown, in single letter format for ease of comparison, in Table 1 along with other Kunitz type trypsin inhibitors. The homology, complete and positive, of the amino acid sequence of PmLTI and the other inhibitors can be seen from the Table. The Edman degradation method was used for amino acid sequencing. The sequencing was performed on an Applied Biosystems 477A Protein Sequencer having a 120A Analyzer. Table 1 shows that over 40% of the N-terminal sequence of PmLTI is identical to the sequences of other Mimosecese trypsin inhibitors (see Table 1, Notes 1–5) and over 60% is homologous.

TABLE 1

N-terminal sequence of PmLTI and homologs

| Inhibitor | Sequence | % ID | % Pos |
|---|---|---|---|
| PmLTI | EVVFDFKGDMMRNGGHYYFFPAAPYGGGNLLAAAV | — | — |
| AC[1] | KELLDADGDILRNGGAYYILPALRGKGGGLTLAKT | 43 | 69 |
| PJ[2] | QELLDVDGEILRNGGSYYILPAFRGKGGGLELAKT | 40 | 69 |
| WB[3] | EPLLDSEGELVRNGGTYYLLPDRWALGGGIEAAAT | 43 | 54 |
| SB[4] | DFVLDNEGNPLENGGTYYILSDITAF-GGIRAAPT | 31 | 40 |
| AP[5] | RELLDVDGNFLRGGSYYIVPAFRGKGGGLELARTG | 40 | 60 |

Notes:
(See also References and Terminology and Abbreviations)
[1]AC = *Acacia confusa* TI, see Ref 32 and Sequence ID. No. 2.
[2]PJ = *Prosopsis jukiflora* TI, see Ref. 21 and Sequence ID No. 3.
[3]WB = Winged bean TI, see Ref. 33 and Sequence ID. No. 4.
[4]SB = Soybean TI, see Ref 17 and Sequence ID. Nos. 5 and 7.
[5]AP = *Adenanthera pavonina* TI, see Ref. 29 and Sequence ID. No. 6.

Enzymatic Assay of the Inhibitory Activity of Pm TIs

The inhibitory activity of *P. macroloba* TIs was determined by enzymatic assay using the method and materials described by Chun et al. (6) which include the procedures of Lenz et al. (34), Terra et al. (35), Takesue et al. (36), McEwen et al. (37), Myrtle and Zell (38) and Thomas and Nation (39). For these enzyme inhibition studies, plant extracts (1.3–20 mg protein/ml) were incubated with appropriate amounts of buffer and bovine trypsin or *Heliocoverpa zea* (H. zea) midgut trypsin at 27° C. The substrates were then added and the reactions were performed as described in the referenced method(s).

The results of inhibitory activity assays of the *P. macroloba* TIs against bovine and *H. zea* trypsins are given in Table 2. While PmLTI inhibited both bovine and *H. zea* trypsin, the results shown in Table 2 indicate that PmLTI was more active against *H. zea* trypsin. The specific activity values were 2.78 IU/mg TI for bovine trypsin and 3.93 IU/mg TI for *H. zea* midgut trypsin. The specific activity of PmSTI was 50.94 IU/mg TI for bovine trypsin and 14.23 IU/mg TI for *H. zea*. PmTIs obtained from the fully active trypsin affinity column (TAC) show lower trypsin inhibition activity than PmTIs obtained from the anhydrotrypsin affinity column (ATAC). This suggests that PmTI is modified by trypsin in such a manner as to reduce the inhibitory effectiveness of the PmTI. It was also found that PmTI was completely bound to trypsin in about 10 minutes. If PmTI, trypsin and column substrate were mixed together at the same time, the PmTI was less deactivated, that is, showed higher trypsin inhibition, than when PmTI and trypsin were incubated together for 10 minutes prior to adding substrate.

TABLE 2

Inhibitory Activity of PmTIs and Soybean TI

| | | Bovine Tr.[1] | | H. zea Midgut Tr[1] | |
|---|---|---|---|---|---|
| Sample | Protein (mg) | IA[2] | SA[3] | IA[2] | SA[3] |
| A[4] | 3.1 | 0.119 | 0.038 | 0.245 | 0.079 |
| B[5] | 2.0 | 4.959 | 2.48 | 7.457 | 3.729 |
| C[6] | 2.0 | 5.567 | 2.784 | 7.855 | 3.928 |
| D[7] | 0.6 | 30.566 | 50.940 | 8.538 | 14.230 |
| E[8] | N/A | N/A | 1.016 | N/A | 0.845 |
| F[9] | N/A | N/A | 5.030 | N/A | 2.101 |

Notes:
[1]Tr = trypsin
[2]IA = Inhibitory Activity in IUs.
[3]SA = Specific Activity in IU/mg protein.
[4]A = Crude Extract.
[5]B = Affinity purified TI.
[6]C = PmLTIs.
[7]D = PmSTIs.
[8]E = Kunitz TI.
[9]F = Bowman-Birk TI.

Biological Assays with PmTIs.

Neonate insect pests were reared on artificial diets containing PmTIs, either crude or purified as taught herein, which were either topically applied to the diet surface or incorporated into the diet as taught by Czapla and Lang (40). The culture tray used in the bioassays were divided into treatment groups. One or a plurality of PmTIs were screen in each tray, each PmTI being applied to a plurality of cells. Each cell was infested with one neonate larvae. A Mylar film with ventilation holes was affixed to the top of each tray to prevent escape.

For the topical assays, the TI was prepared in 0.1M phosphate buffered saline (PBS) buffer (pH 7.8) as a 2% solution. Seventy-five microliters of solution were pipetted onto Stoneville medium in each cell. The culture tray was rotated to ensure equal distribution of the inhibitor. The cells were infected and sealed as described above. The control was 75 ml of 0.1M PBS per cell.

For the diet incorporation assays, Stoneville medium was prepared in standard fashion but with only 90% of the prescribed water. PmTI was added such that the amount in the diet was in the range of 1–5 mg/g. The control treatment consisted of 0.9 ml PBS buffer added to 8.1 g of medium. The medium was poured into the cells and the cells were then infested and covered as described above. Insect weights (Weight or Avg. Wt.) were determined at Day 7 and are given in Tables 3–5.

The data in Table 5 were obtained using corn rootworm (CRW) neonate larvae. The data indicates that PmLTI is effective against CRW whereas PmSTI is not.

TABLE 3

European Corn Borer Bioassay with PmTIs.

| mg TI/cup | Avg. Wt. | % Wt. Change | % Mortality |
|---|---|---|---|
| A. Topical application - Weights at Day 7. | | | |
| 0 | 4.93 mg | — | 6.25 |
| 10 | 4.55 mg | −7.7 | 6.25 |
| 25 | 3.99 mg | −19.1 | 6.25 |
| 50 | 3.86 mg | −21.7 | 6.25 |
| B. Incorporated into diet - Weights at Day 7 | | | |
| Assay 1 | | | |
| 0 | 5.07 mg | — | 6.25 |
| 50 | 6.45 mg | +27.2 | 18.75 |
| 100 | 3.35 mg | −33.9 | 6.25 |
| 250 | 4.18 mg | −17.6 | 25.00 |
| Assay 2 | | | |
| 0 | 4.88 mg | — | 25.00 |
| 100 | 3.41 mg | −30.1 | 18.75 |
| 250 | 2.97 mg | −39.1 | 6.25 |
| 500 | 2.71 mg | −44.5 | 43.75 |

TABLE 4

H. zea Bioassay with PmTIs.
Incorporated into Diet - Weight at Day 7

| mg/ml | Avg. Wt. | % Wt. Change |
|---|---|---|
| Assay 1 | | |
| 0 | 92 mg | — |
| 1.5 | 101 mg | +9.9 |
| 3.0 | 101 mg | +9.8 |
| 6.0 | 54 mg | −41.31[1] |
| Assay 2 | | |
| 0 | 56 mg | — |
| 3 | 55 mg | −1.8 |
| 6 | 56 mg | 0 |
| 9 | 36 mg | −35.7 |
| Assay 3 | | |
| 0 | 182 mg | — |
| 10 | 198 mg | +8.8 |
| 45 | 243 mg | +33.5 |

Note: [1]Comparison significant at the 0.05 level with Sheffe's test.

TABLE 5

Corn Rootworm Bioassay with PmLTI and PmSTI*

| PmTI, mg/ml | Weight | % Loss v. Control | % Mortality |
|---|---|---|---|
| Control, 0 | 2.8 | — | 7 |
| LTI, 0.2 | 2.8 | 0 | 29 |
| LTI, 0.3 | 2.8 | 0 | 36 |
| LTI, 0.8 | 0.7 | 83 | 57 |
| Control, 0 | 3.2 | — | 0 |
| STI, 0.6 | 3.2 | 0 | 0 |

Notes: * = Assay conducted with corn rootworm (CRW) neonate larvae. The PmLTI and PmSTI were incorporated into the diet as described above.

Trypsin Inhibitor Comparisons

Tables 6, 7 and 8 compare PmTI to Bowman-Kirk and Kunitz trypsin inhibitors. The results for bovine chymotrypsin in Table 6 indicate that the activity of PmTI falls between that of Bowman-Kirk and Kunitz, the Bowman-Kirk TI being the least active. The results for the inhibition of H. zea midgut trypsin in Table 7 indicate that the activity of PmTI at pH 8.0 lies between that of the Bowman-Kirk and Kunitz inhibitors, and at pH 9.5 and 10.0 PmTI has a higher level of activity. The results for the inhibition of bovine trypsin in Table 8 indicate that the activity of PmTI falls between that of the Bowman-Kirk and Kunitz TIs.

TABLE 6

Micrograms of Trypsin Inhibitors to Inhibit 1.6 mg Bovine Chymotrypsin by 50%

| | P. macroloba TI | Bowman-Kirk TI | Kunitz TI |
|---|---|---|---|
| pH 8.0* | 8.6 | 1.3 | 11.8 |
| pH 9.0* | 4.4 | 1.0 | 8.4 |
| pH 9.5* | 2.1 | 1.0 | 23.6 |

Note: * = All solutions are 0.1 M Tris-Cl.

TABLE 7

Nanograms of Trypsin Inhibitors to Inhibit H. zea Midgut Trypsin by 50%

| | P. macroloba TI | Bowman-Kirk TI | Kunitz TI |
|---|---|---|---|
| pH 8.0* | 660 | 744 | 323 |
| pH 9.5* | 939 | 974 | 1467 |
| pH 10.0* | 925 | 1196 | 1401 |

Note: * = All solutions are 0.1 M Tris-Cl.

TABLE 8

Nanograms of Trypsin Inhibitors to Inhibit 5 mg Bovine Trypsin by 50%

| | P. macroloba TI | Bowman-Kirk TI | Kunitz TI |
|---|---|---|---|
| pH 8.0* | 835 | 754 | 1551 |
| pH 8.0* | 765 | 637 | 1071 |
| pH 8.0* | 787 | 754 | 1264 |

Note: * = All solutions are 0.1 M Tris-Cl.

The data and descriptions presented herein are for the purpose of describing the invention and are not to be taken as limiting. Other rain forest plants, or plants from other locations, can be and have been evaluated with regard to their production of trypsin inhibitors as described herein. It is within the scope of this invention that those skilled in the art, using the teachings herein, will be able to extract, purify and isolate, from rain forest and other locations, plant trypsin inhibitors analogous to the PmLTI and PmSTI, or mixtures thereof, described herein.

Transgenic Uses

Those skilled in the art of plant genetics, using the genetic techniques which have been developed over the last several decades, can transfect the gene encoding for the production of the PmTIs into the genetic code of food crops such as corn, soybeans, squashes, and similar food crops. Expression of the gene encoding the P. macroloba trypsin inhibitors will enable the crops to produce the PmTI compounds and thus protect themselves against attack by insect pest such as those described herein. Methods for producing transgenic plants are well known to those skilled in the art. For example, one may use, among others known to those skilled in the art, the teachings of Koziel et al., BIO/TECHNOLOGY 11: 194 200 (1993), Vaeck et al., *Nature* 327: 33–37 (1987), Hilder et al., *Transgenic Research* 4: 18–25 (1995) and *Nature* 330: 160–167 (1987), and Johnson et al., *Proc. Natl. Acad. Sci.* 86: 9871–9875, all of which are incorporated herein by reference.

We claim:

1. A purified trypsin inhibitor obtained from *Pentaclethra macroloba* comprising the steps of extracting sliced seeds from said *Pentaclethra macroloba*, extracting said sliced seeds with water to obtain a crude extract and purifying the crude extract to obtain trypsin inhibitor consisting of a plurality of active components whose molecular weights are in the ranges of 38–45 and 6–9 kDa.

2. A trypsin inhibitor in accordance with claim 1, said inhibitor having two isoforms of molecular weight in the range 39–43 kDa.

3. A trypsin inhibitor in accordance with claim 1, said inhibitor having two isoforms of molecular weight in the range 6–9 kDa.

4. A trypsin inhibitor according to claim 2, said inhibitor retaining its trypsin inhibition activity after heating in aqueous solution at approximately 100° C. for 30 minutes.

5. A process for protecting plants against insect attack comprising exposing said insects to an insecticidal protein as claimed in claim 1.

6. A process for protecting plants against insect attack comprising exposing said insects to an insecticidal protein as claimed in claim 2.

7. A process for protecting plants against insect attack comprising exposing said insects to an insecticidal protein as claimed in claim 3.

8. An insecticidal protein comprising trypsin inhibitors obtainable from *Pentaclethra macroloba*, said inhibitors being approximately 38–45 and 6–9 kilodaltons (kDa) in size, wherein said 38–45 kDa species consists of a 43 kDa species having a N-terminus amino acid sequence identified as Sequence ID. No. 1: Glu-Val-Val-Phe-Asp-Phe-Lys-Gly-Asp-Met-Met-Arg-Asn-Gly-Gly-His-Tyr-Tyr-Phe-Phe-Pro-Ala-Ala-Pro-Tyr-Gly-Gly-Gly-Asn-Leu-Leu-Ala-Ala-Ala-Val.

9. An insecticidal protein comprising trypsin inhibitors obtainable from *Pentaclethra macroloba*, said inhibitors being approximately 38–45 and 6–9 kilodaltons (kDa) in size.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

```
Glu Val Val Phe Asp Phe Lys Gly Asp Met Met Arg Asn Gly Gly His
 1               5                  10                  15

Tyr Tyr Phe Phe Pro Ala Ala Pro Tyr Gly Gly Gly Asn Leu Leu Ala
            20                  25                  30

Ala Ala Val
         35
```

( 2 ) INFORMATION FOR SEQ ID NO:2:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

```
Lys Glu Leu Leu Asp Ala Asp Gly Asp Ile Leu Arg Asn Gly Gly Ala
 1               5                  10                  15

Tyr Tyr Ile Leu Pro Ala Leu Arg Gly Lys Gly Gly Gly Leu Thr Leu
            20                  25                  30

Ala Lys Thr
         35
```

( 2 ) INFORMATION FOR SEQ ID NO:3:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

```
Gln Glu Leu Leu Asp Val Asp Gly Glu Ile Leu Arg Asn Gly Gly Ser
 1               5                  10                  15

Tyr Tyr Ile Leu Pro Ala Phe Arg Gly Lys Gly Gly Gly Leu Glu Leu
            20                  25                  30

Ala Lys Thr
         35
```

( 2 ) INFORMATION FOR SEQ ID NO:4:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

```
Glu Pro Leu Leu Asp Ser Glu Gly Glu Leu Val Arg Asn Gly Gly Thr
 1               5                   10                  15

Tyr Tyr Leu Leu Pro Asp Arg Trp Ala Leu Gly Gly Gly Ile Glu Ala
            20                  25                  30

Ala Ala Thr
        35
```

( 2 ) INFORMATION FOR SEQ ID NO:5:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

```
Asp Phe Val Leu Asp Asn Glu Gly Asn Pro Leu Glu Asn Gly Gly Thr
 1               5                   10                  15

Tyr Tyr Ile Leu Ser Asp Ile Thr Ala Phe
            20                  25
```

( 2 ) INFORMATION FOR SEQ ID NO:6:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( x i ) SEQUENCE DESCRIPTION: SEQ ID NO:6:

```
Arg Glu Leu Leu Asp Val Asp Gly Asn Phe Leu Arg Gly Gly Ser Tyr
 1               5                   10                  15

Tyr Ile Val Pro Ala Phe Arg Gly Lys Gly Gly Gly Leu Glu Leu Ala
            20                  25                  30

Arg Thr Gly
        35
```

( 2 ) INFORMATION FOR SEQ ID NO:7:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:7:

```
Gly Gly Ile Arg Ala Ala Pro Thr
 1               5
```